(12) United States Patent
Tsuchiya

(10) Patent No.: US 6,413,501 B2
(45) Date of Patent: *Jul. 2, 2002

(54) PLAQUE-INHIBITING ORAL COMPOSITIONS

(75) Inventor: Rie Tsuchiya, Birkerød (DK)

(73) Assignee: Novozymes A/S, Bagsvaerd (DK)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/173,935

(22) Filed: Oct. 16, 1998

Related U.S. Application Data

(60) Provisional application No. 60/065,944, filed on Oct. 27, 1997.

(30) Foreign Application Priority Data

Oct. 17, 1997 (DK) .............................................. 1191/97

(51) Int. Cl.$^7$ .................................................. A61K 7/28
(52) U.S. Cl. ....................................... 424/50; 424/94.61
(58) Field of Search ........................ 424/50, 94.2, 94.61

(56) References Cited

U.S. PATENT DOCUMENTS

| | | | |
|---|---|---|---|
| 3,194,738 A | | 7/1965 | Harrison et al. |
| 4,138,476 A | * | 2/1979 | Simonson et al. ............. 424/50 |
| 4,255,414 A | * | 3/1981 | Lembke et al. ................ 424/50 |
| 4,353,891 A | | 10/1982 | Guggenheim et al. |
| 4,430,322 A | * | 2/1984 | Stoudt et al. .................. 424/49 |
| 4,438,093 A | * | 3/1984 | Shimada et al. ............... 424/50 |
| 4,469,673 A | * | 9/1984 | Iioka et al. .................... 424/50 |
| 4,486,330 A | * | 12/1984 | Yoshida et al. .......... 252/174.12 |
| 4,576,816 A | * | 3/1986 | Suganuma et al. ............ 424/50 |
| 4,740,368 A | | 4/1988 | Plevy |
| 5,085,851 A | * | 2/1992 | Okada et al. .................. 424/50 |
| 5,145,665 A | | 9/1992 | Klueppel et al. |
| 5,320,830 A | | 6/1994 | Lukacovic et al. |
| 5,437,856 A | * | 8/1995 | Lukacovic et al. ........... 424/50 |
| 5,747,005 A | * | 5/1998 | Barels et al. .................. 424/50 |
| 5,853,702 A | * | 12/1998 | Berka et al. ................... 424/50 |
| 6,159,447 A | * | 12/2000 | Budny et al. .................. 424/49 |

FOREIGN PATENT DOCUMENTS

| | | |
|---|---|---|
| DE | 1948 468 | 4/1971 |
| EP | 0 787 482 A1 | 8/1997 |
| FR | 7.314 M | 8/1967 |
| FR | 2132980 | 11/1972 |
| FR | 2 651 433 | 3/1991 |
| GB | 1284728 * | 8/1972 |
| GB | 1284 728 | 8/1972 |
| GB | 2 206 585 | 1/1989 |
| KR | 9609510 * | 7/1996 |
| LU | 59502 | 9/1969 |
| WO | WO 97/06775 | 2/1997 |
| WO | WO 98/57653 | 12/1998 |

OTHER PUBLICATIONS

JP 8012544 (English Abstract only).
Guggenheim et al., Caries Res. 6:289–297 (1972).
Abstr. JP XP–0020098186.

* cited by examiner

*Primary Examiner*—Ralph Gitomer
(74) *Attorney, Agent, or Firm*—Elias Lambiris

(57) ABSTRACT

The present invention relates to oral compositions comprising plaque-inhibiting or plaque-removing enzymes, in particular at least one starch-hydrolysing enzyme, e.g. an α-amylase or a debranching enzyme such as a pullulanase, and/or at least one starch-modifying enzyme, e.g. a transglucosidase or a CGTase, and to a method for inhibiting plaque formation or removing plaque using such oral compositions.

40 Claims, 1 Drawing Sheet

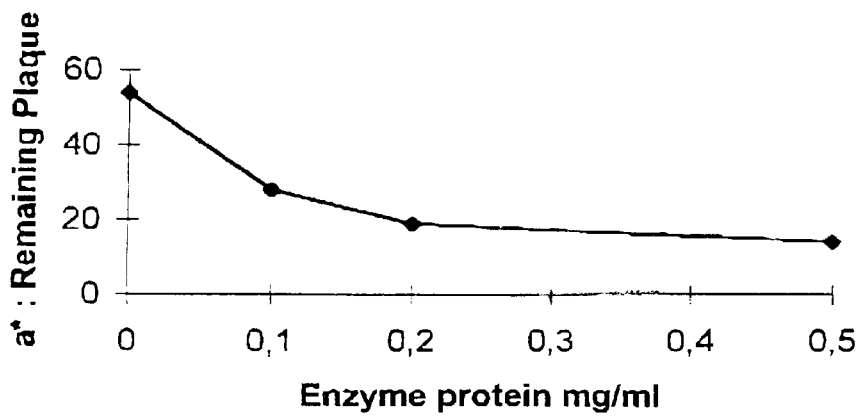
Figure 1. Plaque inhibition/prevention effect of Fungamyl™
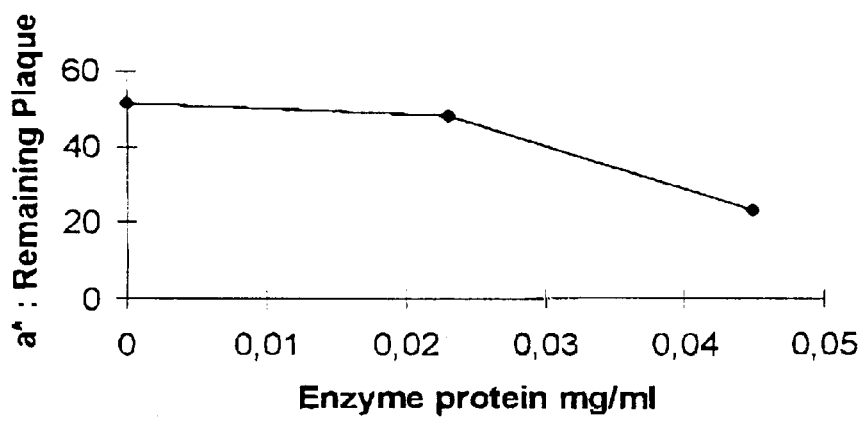
Figure 2. Plaque inhibition/prevention effect of Promozyme™
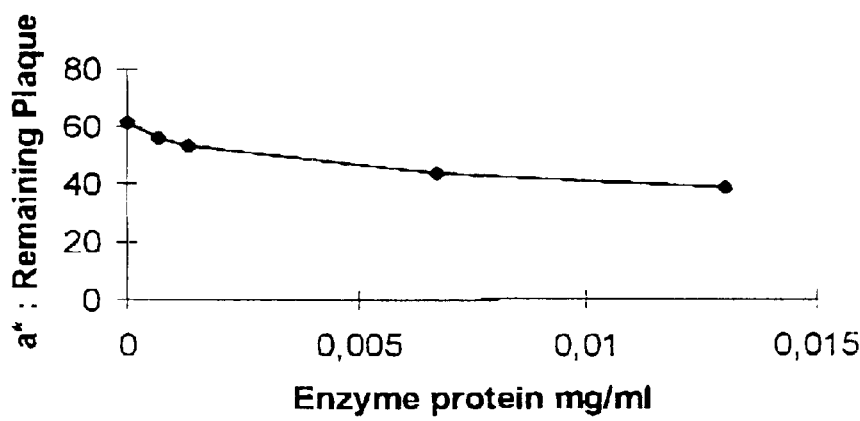
Figure 3. Plaque inhibition/prevention of Maltogenase™

PLAQUE-INHIBITING ORAL COMPOSITIONS

This application claims priority from Provisional application Ser. No. 60/065,944, filed Oct. 27, 1997.

FIELD OF THE INVENTION

The present invention relates to oral compositions comprising plaque-inhibiting or plaque-removing enzymes and to a method for inhibiting plaque formation or removing plaque using such oral compositions.

BACKGROUND OF THE INVENTION

Dental plaque is a mixture of bacteria, epithelial cells, leukocytes, macrophages and other oral exudates that forms on the surface of unclean teeth. The bacteria produce highly branched polysaccharides which together with microorganisms from the oral cavity form an adhesive matrix for the continued proliferation of plaque. Left untreated, the formation of dental plaque will eventually lead to dental caries, gingival inflammation, periodontal disease, and eventually tooth loss. As plaque continues to accumulate, rock-hard white or yellowish deposits arise. These deposits are called calcified plaque, calculus or tartar, and are formed in the saliva from plaque and minerals, in particular calcium.

Oral polysaccharides are produced from sucrose introduced into the mouth, e.g. as a food or beverage constituent, by the action of cariogenic microorganisms such as *Streptococcus mutans* or *Streptococcus sanguis* growing in the oral cavity. These oral polysaccharides comprise water-soluble dextran having primarily $\alpha$-1,6 glucosidic linkages, and a major component of water-insoluble extracellular polysaccharides called "mutan" comprised of a backbone with $\alpha$-1,3-glycosidic linkages and branches with $\alpha$-1,6-glycosidic linkages. Mutan binds to hydroxyapatite (constituting the hard outer porous layer of the teeth) and to acceptor proteins on the cell surface of said cariogenic bacteria adhering to the teeth surface.

Numerous attempts have been made to combat this process by either eliminating the plaque or by altering the environment by changing the composition of the plaque, and many toothpastes and other oral care compositions have, with varying success, aimed at removing or inhibiting plaque. The goal of effectively inhibiting plaque in particular has remained elusive, however, and the need remains for oral care compositions that in normal use are effective at inhibiting plaque formation and the accompanying dental diseases that can result from plaque formation.

WO 97/06775 discloses oral compositions comprising an oxidoreductase, and optionally a dextranase and/or a mutanase, for bleaching of teeth, but no plaque-inhibiting or plaque-removing effects of such compositions are described or suggested.

To prevent the formation of dental caries, plaque and tartar, it has been suggested to add a dextranase and/or a mutanase and/or other enzymes to oral care compositions and products.

JP patent publication 8012544 (Lion) describes a plaque preventing effect of dextranase, mutanase and triclosan and/or biosol.

U.S. Pat. No. 4,353,891 (Guggenheim et al.) concerns plaque removal using mutanase from *Trichoderma harzianum* CBS 243.71 to degrade mutan synthesized by cultivating *Streptococcus mutans* strain CBS 350.71 identifiable as OMZ 176. It is stated that the critical ingredient in dental plaque is a water-insoluble polysaccharide with $\alpha$-1,3-glucosidic bonds and that such polysaccharide material termed mutan is not attacked by dextranase.

Guggenheim et al. (1972), Caries Res. 6, p. 289–297, disclose that the extent of dental plaque of rats is not significantly affected by the simultaneous use of a dextranase and a 1,3-glucanase (mutanase).

Hare et al. (1978), Carbohydrate Research 66, p. 245–264, found that a synergistic effect is obtained when hydrolysing and solubilizing oral glucans with a bacterial dextranase in combination with bacterial $\alpha$-1,3 glucanase from *Cladosporium resinae*.

U.S. Pat. No. 4,438,093 (The Research Foundation for Microbial diseases of Osaka) describes oral compositions comprising a dextranase and a $\alpha$-1,3-glucanase (mutanase), both being present in an amount of 0.5 to 100 enzyme units per gram of said oral composition, in an enzyme unit ratio of 1:2 to 2:1. Said dextranase is derived from a bacteria within the genus Corynbacterium and said $\alpha$-1,3-glucanase is derived from a bacteria within the genus Pseudomonas, GB 2,206,585 (Dental Chem Co. Ltd.) describes a toothcleaning agent containing hydroxyapatite as a polishing agent, with a laevanase, dextranase and mutanase immobilized on the hydroxyapatite.

U.S. Pat. No. 5,145,665 (Henkel) discloses a composition for the care of the mouth and teeth comprising a dextranase and/or $\alpha$-1,3-glucanase for cleaving polysaccharides in the mouth.

FR 2,651,433 (DANA) concerns dentifrice products containing a dextranase to act on recent plaque, a mutanase to act on old and insoluble plaque, and a mixture of other enzymes having bactericidal action U.S. Pat. No. 5,320,830 (Proctor & Gamble) describes toothpaste compositions for the reduction of plaque and gingivitis comprising a) a surfactant, b) an enzyme, c) a chelating agent d) a fluoride source, e) a silica abrasive and f) a carrier. The enzyme is an endoglucanase, papain, a dextranase and/or a mutanase.

It has now surprisingly been found that oral care compositions comprising one or more starch-hydrolysing or starch-modifying enzymes are effective for inhibiting/preventing dental plaque formation and/or for removing plaque.

SUMMARY OF THE INVENTION

The object of the present invention is thus to provide oral compositions that are effective for inhibiting/preventing plaque formation and for removing plaque, as well as a method for inhibiting plaque formation or for removing plaque.

A first aspect of the invention thus relates to an oral care composition comprising a plaque-inhibiting and/or plaque-removing effective amount of at least one starch-hydrolysing enzyme and/or at least one starch-modifying enzyme.

In a second aspect, the invention relates to a method for inhibiting plaque formation or removing plaque, comprising contacting the teeth and/or gums with an oral care composition comprising a plaque-inhibiting and/or plaque-removing effective amount of at least one starch-hydrolysing enzyme and/or at least one starch-modifying enzyme for a period of time to obtain a plaque-inhibiting or plaque-removing effect.

BRIEF DESCRIPTION OF THE DRAWING

FIG. 1 shows the plaque-inhibiting effect of FUNGAMYL.

FIG. 2 shows the plaque-inhibiting effect of PROMOZYME.

FIG. 3 shows the plaque-inhibiting effect of MALTOGENASE.

DETAILED DESCRIPTION OF THE INVENTION

The term "starch-hydrolysing enzyme" in the context of the present application refers to any enzyme, such as an α-amylase (E.C. 3.2.1.1), which functions to hydrolyse linkages in starch.

The term "starch-modifying enzymes" used in the context of the invention refers to the group of enzymes within E.C. 2.4.1., and includes in particular transglycosidases (E.C. 2.4.1.18) and CGTases (E.C. 2.4.1.19).

The inventors have found that dental plaque can be inhibited/prevented or removed by the use of at least one starch-hydrolysing enzyme and/or at least one starch-modifying enzyme. Said effect of such enzymes has not been foreseen before.

In the first aspect the invention relates to an oral care composition comprising a plaque-inhibiting and/or plaque-removing effective amount of at least one starch-hydrolysing enzyme and/or at least one starch-modifying enzyme.

In an embodiment of the invention the starch-modifying enzyme is a CGTase (E.C. 2.4.1.19) or a transglucosidase (2.4.1.18).

When the starch-modifying enzyme is a CGTase, it may be derived from a strain of *Bacillus autolyticus*, a strain of *Bacillus cereus*, a strain of *Bacillus circulans*, a strain of *Bacillus circulans* var. alkalophilus, a strain of *Bacillus coagulans*, a strain of *Bacillus firmus*, a strain of *Bacillus halophilus*, a strain of *Bacillus macerans*, a strain of *Bacillus megaterium*, a strain of *Bacillus ohbensis*, a strain of *Bacillus stearothermophilus*, a strain of *Bacillus subtilis*, a strain of *Klebsiella pneumoniae*, a strain of Thermoanaerobacter sp, a strain of *Thermoanaerobacter ethanolicus*, a strain of *Thermoanaerobacter finnii*, a strain of *Clostridium thermoamylolyticum*, a strain of *Clostridium thermosaccharolyticum*, or a strain of *Thermoanaerobacterium thermosulfurigenes*.

When the starch-modifying enzyme is a transglucosidase, it may be derived from *Aspergillus niger*, e.g. the product sold by Amamo Pharmaceutical Co., Japan.

In another embodiment of the invention the oral care composition comprises a starch-hydrolysing enzyme.

This will typically be an α-amylase, such as a bacterial α-amylase, such as BAN™ or Maltogenase™ (both available from Novo Nordisk), or an α-amylase derived from *Bacillus subtilis*; an α-amylase derived from *Bacillus amyloliquefaciens*; an α-amylase derived from *Bacillus stearothermophilus*; an α-amylase derived from *Aspergillus oryzae*; or an α-amylase derived from a non-pathogenic microorganism.

The α-amylase may also be a fungal α-amylase, such as Fungamyl™, which is available from Novo Nordisk.

The starch-hydrolysing enzyme may in another embodiment of the invention be a debranching enzyme, in particular a pullulanase (E.C. 3.2.1.41), such as Promozyme™.

In a preferred embodiment the oral care composition comprises at least one starch-modifying enzyme as defined above, in particular a CGTase, and a mutanase and/or a dextranase.

In another preferred embodiment the oral care composition of the invention comprises at least one starch-hydrolysing enzyme as defined above, in particular a bacterial α-amylase, and a mutanase and/or a dextranass.

The mutanase may be derived from a strain of Trichodermna sp., in particular *T. harzianum*, especially *T. harzianum* CBS 243.71 (available from Novo Nordisk).

The dextranase may be derived from a strain of Paecilomyces sp., in particular *Paecilomyces lilacinus* (available from Novo Nordisk).

In a second aspect the invention relates to an oral care product comprising an oral care composition of the invention.

An "oral care product" of the invention is defined as a product which can be used for maintaining and/or improving oral hygiene in the mouth of humans and animals, and/or preventing or treating dental diseases.

Examples of such oral care products include toothpastes, dental creams, gels or tooth powders, odontics, mouthwashes, denture cleaning agents, pre- or post-brushing rinse formulations, chewing gum and lozenges. An oral care product may also be in the form of a dental floss or toothpick.

Toothpastes and tooth gels typically include abrasive polishing materials, foaming agents, flavouring agents, humectants, binders, thickeners, sweeteners and water. As used herein, the term "toothpaste" is intended to refer to formulations in the form of both pastes and gels.

Mouthwashes typically comprise a water/alcohol solution, flavouring agents, humectants, sweeteners, foaming agents and colorants.

A chewing gum according to the invention may be prepared in a manner known per se by incorporating one or more enzymes into a conventional chewing gum base, e.g. based on chicle and/or one or more additional synthetic or natural polymers, and containing e.g. natural and/or artificial sweeteners, flavourings, etc. as desired. Upon addition of the enzyme(s) to the gum base, the temperature of the gum base should not be too high, e.g. preferably not more than about 60° C., more preferably not more than about 50° C.

Abrasive polishing materials for use in oral care products according to the invention include alumina and hydrates thereof, such as alpha alumina trihydrate. magnesium trisilicate, magnesium carbonate. sodium bicarbonate ("baking soda"), kaolin, aluminosilicates, such as calcined aluminum silicate and aluminum silicate, calcium carbonate, zirconium silicate, and also powdered plastics, such as polyvinyl chloride, polyamides, polymethyl methacrylate, polystyrene, phenol-formaldehyde resins, melamine-formaldehyde resins, urea-formaldehyde resins, epoxy resins, powdered polyethylene, silica xerogels, hydrogels and aerogels and the like. Also suitable as abrasive agents are calcium pyrophosphate, water-insoluble alkali metaphosphates, dicalcium phosphate and/or its dihydrate, dicalcium orthophosphate, tricalcium phosphate, particulate hydroxyapatite and the like. It is also possible to employ mixtures of these substances.

Depending on the nature of the oral care product, the abrasive product may be present in an amount of from 0 to 70% by weight, preferably from 1% to 70%. For toothpastes, the abrasive material content typically lies in the range from 10% to 70% by weight of the final toothpaste product.

Humectants are employed to prevent loss of water from e.g. toothpastes. Suitable humectants for use in oral care products according to the invention include the following compounds and mixtures thereof: glycerol, polyol, sorbitol, polyethylene glycols (PEG), propylene glycol, 1,3- propanediol, 1,4-butane-diol, hydrogenated partially hydrolysed polysaccharides and the like. Humectants are in general present in an amount of from 0% to 80%, preferably 5 to 70% by weight in a toothpaste.

Examples of suitable thickeners and binders which help stabilize the dentifrice product are silica, starch, tragacanth gum, xanthan gum, extracts of Irish moss, alginates, pectin, cellulose derivatives, such as hydroxyethyl cellulose, sodium carboxymethyl cellulose and hydroxy-propyl cellulose, polyacrylic acid and its salts and polyvinyl-pyrrolidone. Thickeners may be present in toothpastes, creams and gels in an amount of from 0.1 to 20% by weight, and binders in an amount of from 0.01 to 10% by weight of the final product.

As a foaming agent soap, anionic, cationic, non-ionic, amphoteric and/or zwitterionic surfactants can be used. These may be present at levels of from 0 to 15%, preferably from 0.1 to 13%, more preferably from 0.25 to 10% by weight of the final product.

Surfactants are only suitable in the context of the present invention to the extent that they do not exert any adverse effect on the activity of the enzymes.

Examples of surfactants include fatty alcohol sulphates, salts of sulphonated monoglycerides or fatty acids having from 10 to 20 carbon atoms, fatty acid-albumin condensation products, salts of fatty acids amides and taurines and/or salts of fatty acid esters of isethionic acid.

Suitable sweeteners include saccharin and/or other sweeteners suitable for use in oral care products.

Flavouring agents, such as spearmint and peppermint, are usually present in low amounts, such as from 0.01% to about 5% by weight, especially from 0.1% to 5%.

Water is usually added in an amount giving e.g. a toothpaste a flowable form, i.e. an amount of from 40% to 70% by weight of the final product.

In addition, water-soluble anti-bacterial agents, such as chlorhexidine digluconate, hexetidine, alexidine, quaternary ammonium anti-bacterial compounds and water-soluble sources of certain metal ions such as zinc, copper, silver and stannous ions (e.g. zinc, copper and stannous chloride, and silver nitrate) may also be included.

Also contemplated according to the invention is the addition of other anti-calculus agents, anti-plaque agents other than the enzymes which are the subject of the present application, compounds which can serve as a fluoride source, dyes/colorants, preservatives, vitamins, pH-adjusting agents, anti-caries agents, desensitizing agents, etc.

A toothpaste produced from an oral composition of the invention may e.g. comprise the following ingredients (in weight % of the final toothpaste composition):

| Abrasive material | 10 to 70% |
| --- | --- |
| Humectant | 0 to 80% |
| Thickener | 0.1 to 20% |
| Binder | 0.01 to 10% |
| Sweetener | 0.1% to 5% |
| Foaming agent | 0 to 15% |
| Starch-degrading enzyme(s) and/or starch-modifying enzyme(s) | 0.0001% to 20% |
| Other enzymes | 0 to 20% |
| Peroxide | 0 to 1% |

A mouthwash produced from an oral care composition of the invention may e.g. comprise the following ingredients (in weight % of the final mouthwash composition):

| 0–20% | Humectant |
| --- | --- |
| 0–2% | Surfactant |
| 0–5% | Starch-degrading enzyme(s) and/or starch-modifying enzyme(s) |
| 0–5% | Other enzymes |
| 0–20% | Ethanol |
| 0–2% | Other ingredients (e.g. flavour, sweetener or other active ingredients such as fluorides). |
| 0–70% | Water |

The mouthwash composition may be buffered with an appropriate buffer, e.g. sodium citrate or phosphate in the pH-range 6–7.5.

The mouthwash may be in non-diluted form (i.e. to be diluted before use) or in diluted (ready-to-use) form.

The oral care compositions and products of the present invention can be made using methods which are common in the oral product field.

The invention further relates to the use of one or more starch-hydrolysing enzymes and/or one or more starch-modifying enzymes as described above for the preparation of a composition for the inhibitioniprevention of plaque formation and/or removal of plaque.

An oral care product in solid to flowable form such as a toothpaste will typically be contacted with the teeth and/or gums using a toothbrush or the like. In the case of a liquid oral care product such as a mouthwash, the contact will typically take place by rinsing the mouth.

The time period during which an oral care product according to the invention is contacted with the teeth and/or gums to obtain the desired plaque inhibiting or plaque removing effect can vary according to such factors as the nature of the composition or product and the need of the subject. However, contacting the oral care product with the teeth and/or gums for between about 30 seconds to 15 minutes will normally be sufficient for obtaining the desired result, e.g. contact by brushing the teeth or rinsing the mouth for a period of about 1–3 minutes at a time. This is preferably performed on a regular basis, e.g. 1–3 times a day.

After use, the oral care product is typically removed from the mouth, e.g. by spitting it out, and the mouth may subsequently be rinsed with a liquid such as tap water.

While not wishing to be bound by any particular theory, it is believed that the surprising plaque-inhibiting effect found according to the present invention may be due to the fact that the starch-hydrolysing and/or starch-modifying enzymes react with sucrose to produce a coupling sugar before enzymes produced by the microorganisms gain access to the sucrose. Regardless of the mechanism of action. the plaque-inhibiting effect observed by use of the enzymes in question is surprising and is not believed to have been described or suggested previously.

The invention will be further illustrated in the following non-limiting examples.

MATERIALS AND METHODS

Materials

Dextranase produced by *Paecilomyces lilacinum* (available from Novo Nordisk A/S). Mutanase produced by *Trichoderma harzianum* CBS 243.71 (available from Novo Nordisk A/S)

Maltogenase: Novamyl™ (a bacterial maltogenic α-amylase) available from Novo Nordisk A/S.

Fungamyl™ (a fungal α-amylase) available from Novo Nordisk A/S.

Transglucosidase produced by *Aspergillus niger* (available from Amona Pharmaceuticals Co.).

BAN™ (a bacterial α-amylase) available from Novo Nordisk A/S.

CGTase produced by Thermobacterium sp., available from Novo Nordisk A/S.

Promozyme™ (a bacterial pullulanase) available from Novo Nordisk A/S

Microorganisms

*Streptococcus sobrinus* strain CBS 350.71 identifiable as OMZ 176

*Actinomyces viscosus* DSM 43329

*Fusobacterium nucleatum* subsp. polymorphum DSM 20482

Solutions

Erythrosin B (Sigma)

Equipment

Chromameter CR-200 (Minolta)

Preparation of hydroxyapatite disks

Hydroxyapatite (HA) disks are prepared by compressing 250 mg of hydroxyapatite in a disk die at about 5,900 kg (13,000 lbs) of pressure for 5 minutes. The disks are then sintered at 600° C. for 4 hours and finally hydrated with sterile deionized water.

Sterilisation of hydroxypapatite disks

HA disks are sterilised at 180° C. for two hours.

Mutan preparation

Mutan is prepared by growing *Streptococcus sobrinus* CBS 350.71 at pH 6.5, 37° C. (kept constant), and with an aeration rate of 75 rpm in a medium comprised of the following components;

| | |
|---|---|
| NZ-Case | 6.5 g/l |
| Yeast Extract | 6 g/l |
| $(NH_4)_2SO_4$ | 20 g/l |
| $K_2PO_4$ | 3 g/l |
| Glucose | 50 g/l |
| Pluronic PE6100 | 0.1% |

After 35 hours, sucrose is added to a final concentration of 60 g/l to induce glucosyltransferase. The total fermentation time is 75 hours. The supernatant from the fermentation is centrifuged and filtered (sterile). Sucrose is then added to the supernatant to a final concentration of 5% (pH is adjusted to pH 7.0 with acetic acid) and the solution is stirred overnight at 37° C. The solution is filtered and the insoluble mutan is harvested on Propex and washed extensively with deionized water containing 1% sodium benzoate, pH 5 (adjusted with acetic acid). Finally, the insoluble mutan is lyophilized and ground.

Determination of dextranase activity (KDU)

One Kilo Novo Dextranase Unit (1 KDU) is the amount of enzyme which breaks down dextran forming reducing sugar equivalent to 1 g maltose per hour in the Novo Nordisk method for determination of dextranase based on the following standard conditions:

| | |
|---|---|
| Substrate | Dextran 500 (Pharmacia) |
| Reaction time | 20 minutes |
| Temperature | 40° C. |
| pH | 5.4 |

A detailed description of Novo Nordisk's analytical method (AF 120) is available on request.

Determination of mutanase activity (MU)

One Mutanase Unit (MU) is the amount of enzyme which under standard conditions liberates 1 μmol reducing sugar (calculated as glucose) per minute.

| Standard Conditions | |
|---|---|
| Substrate | 1.5% mutan |
| Reaction time | 15 minutes |
| Temperature | 40° C. |
| pH | 5.5 |

A detailed description of Novo Nordisk's analytical method (AF 180/1-GB) is available from Novo Nordisk A/S on request.

Determination of BAN™ (Bacteria Amylase Novo) activity (KNU) (Kilo Novo-α-amylase Units)

The standard activity is determined relative to an analytical standard under the following conditions:

| | |
|---|---|
| Substrate: | p-nitrophenyl-alpha-D-maltoheptaoside (pNP-G7) |
| Temperature: | 37° C. |
| pH: | 7.1 |

A detailed description of Novo Nordisk's analytical method (Novo Nordisk publication AF215) is available on request.

Determination of Fungamyl® activity (FAU)

One Fungal α-amylase Unit (1 FAU) is the amount of enzyme which breaks down 5.26 g starch (Merck, Amylum solubile Erg. B.6, Batch 9947275) per hour at Novo Nordisk's standard method for determination of α-amylase based upon the following standard conditions:

| | |
|---|---|
| Substrate: | soluble starch |
| Reaction time: | 7–20 minutes |
| Temperature | 37° C. |
| pH: | 4.7 |

A detailed description of Novo Nordisk's method of analysis is available on request.

Determination of Maltogenase activity (MANU)

1 Maltogenic Amylase Novo Unit (MANU) is defined as the amount of enzyme which under standard conditions hydrolyzes 1 μmole of maltotriose per minute. Copies of the analytical method are available on request.

Determination of AMG™ activity (AGU)

One Novo Amyloglucosidase Unit (AGU) is defined as the amount of enzyme which hydrolyzes 1 μmole maltose per minute under the following standard conditions;

| | |
|---|---|
| Substrate: | maltose |
| Temperature: | 25° C. |
| pH: | 4.3 (acetate buffer) |
| Reaction time | 30 minutes |

A detailed description of the analytical method (AF 22) is available on request.

Determination of Transglucosidase activity (AGU)

Transglucosidase activity is determined using the method described above for determining AMG™ activity, and is expressed using the same units (AGU).

Determination of CGTase activity (KNU)

The CGTase KNU enzymatic activity was measured by a slightly modified procedure of the Phadebas amylase test (Pharmacia). Phadebas tablets (Phadebas™ Amylase Test, Pharmacia) are used as a substrate. This substrate is a cross-linked insoluble blue-colored starch polymer, which is mixed with bovine serum albumin and a buffer substance. After suspension in water, starch is hydrolyzed by the enzyme, thereby yielding blue fragments. The determination is carried out after incubation at 60° C., pH 6.2, in 0.15 nM calcium for 15 minutes. The absorbance of the resulting blue solution, determined at 620 nm, corresponds to the enzymatic activity.

The enzyme activity is compared to that of an enzyme standard, and the activity is expressed in the same unit as that of the enzyme standard. The enzyme standard was Termamyl™ (Novo Nordisk A/D, Denmark), the amylolytic activity of which has been be determined using potato starch as a substrate. This method is based on the break-down of modified potato starch by the enzyme, and the reaction is followed by mixing samples of the starch/enzyme solution with an iodine solution. Initially, a blackish-blue color is formed, but during the break-down of the starch the blue color gets weaker and gradually turns into a reddish-brown, which is compared to a colored glass standard. One Kilo Novo α-Amylase Unit (KNU) is defined as the amount of enzyme which, under standard conditions (i.e. at 37° C.+/− 0.05; 0.0003 M $Ca^{2+}$; and pH 5.6) dextrinizes 5.26 g starch dry substance, Merck Amylum soluble. The activity is expressed below in Novo Units (NU) per ml.

CGTase activity was determined by incubating diluted enzyme with substrate in 10 mM sodium citrate, pH 6.0 for 4–10 minutes at 60° C.

Determination of Promozyme™ activity (PUN)

One Pullulanse Unit Novo (PUN) is defined as the amount of enzyme which hydrolyzes pullulan, liberating reducing carbohydrate with a reducing carbohydrate with a reducing power equivalent to 1 μmole glucose per minute under the following standard conditions:

| | |
|---|---|
| Substrate: | 0.2% pullulan |
| Temperature: | 40° C. |
| pH: | 5.0 (0.05M citrate buffer) |
| Reaction time: | 30 minutes |

A detailed description of the analysis method (AF190) is available on request.

Assessment of the plaque inhibition effect

The method used for assessing the plaque removal effect is based on the method described by Kao in JP 2250816. According to the present method, hydroxyapatite disks, sterilised as described above, become coated with a biofilm by being placed overnight in the presence of three strains of oral microorganisms (*Streptococcus sobrinus, Actinomyces viscosus* and *Fusobacterium nucleatum*) and various enzymes in a Brain Heart Infusion Medium (Difco) containing 0.2% sucrose.

To test plaque inhibition effect, 0.1% Erythrosin B in PBS (phosphate buffered saline) is used to stain plaque present on the hydroxyapatite disks red. The intensity of the red colour (referred to as a*) is measured on a Chromameter CR-200. The maximum a* value is 60. Values below that indicate a less intensive red colour (i.e. less plaque present). An a* value of zero indicates no red colouring (ie. no plaque). A plaque inhibition effect is expressed as a relative figure based on the value of a* for a non-treated biofilm being 100%.

EXAMPLES

Example 1

Plaque preventing effect of different starch-hydrolysing enzymes

Three oral microorganisms, *Streptococcus sobrinus, Actinomyces viscosus* and *Fusobacterium nucleatum*, respectively, were cultivated anaerobically overnight at 37° C. in the presence of various enzymes. Hydroxyapatite disks coated with sterilised saliva were immersed in a culture broth during cultivation so that an oral biofilm was formed on the disks. After cultivation, the disks were briefly rinsed with a phosphate buffered saline and then incubated in a 1 ml 0.1% Erythrosin B in PBS for 1 minute to stain plaque present on the hydroxyapatite disks red. The Erythrosin B solution was removed and the disks were rinsed with PRS for a few minutes. The disks were air-dried overnight. The intensity of the red colour (a*) was measured on a Chromameter CR-200 and compared to that of the non-treated disks.

The plaque-prevention results of a number of different enzymes are shown below in Table 1.

TABLE 1

Plaque inhibiting/preventing activity of selected starch-hydrolysing enzymes

| Enzyme | Activity | Plaque intensity (%) |
|---|---|---|
| None (control) | | 100 |
| Maltogenase ™ (bacterial maltogenic α-amylase) | 200 MANU/ml | 36.8** |
| Fungamyl ™ (fungal α-amylase) | 40 FAU/ml | 45.3** |
| Transglucosidase derived from *A. niger* | 32 AGU/ml | 54.2** |
| Promozyme ™ (bacterial pullulanase) | 10 PUN/ml | 45.0* |

*statistically significant, p < 0.01
**statistically significant, p < 0.001

As can be seen in the table above, statistically significant plaque prevention/inhibition effects are obtained with all starch-hydrolysing enzymes at the activity levels listed.

Example 2

Plaque preventing effect of a starch-hydrolysing enzyme a starch-modifying enzyme in combination with a mutanase and a dextranase Three oral microorganisms, *Streptococcus sobrinus, Actinomyces viscosus* and *Fusobacterium nucleatum*, respectively, were cultivated anaerobically overnight at 37° C. in the presence of 1 MU/ml mutanase and 1 KDU/ml dextranase and the enzyme listed in the Table below. Hydroxyapatite disks coated with sterilised saliva were immersed in a culture broth during cultivation so that an oral biofilm was formed on the disks. After cultivation, the disks were treated as describe in Example 1, and the intensity of the red colour was determined.

TABLE 2

Plaque inhibiting/preventing activity of a starch-modifying enzyme and a starch-hydrolysing enzyme together with mutanase and dextranase

| Enzyme | Activity | Plaque intensity (%) |
|---|---|---|
| Control* | | 100 |
| BAN ™ (Bacterial α-amylase) | 12 KNU/ml | 42.7 |
| CGTase | 0.32 KNU/ml | 40.4 |

*: All culture broths contained 1 MU/ml mutanase and 1 kDU/ml dextranase

As can be seen, the use of the two enzymes BAN™ and the CGTase together with a mutanase and a dextranase resulted in an improved plaque inhibition compared to mutanase and dextranase alone. The additional effect of the combination with mutanase and dextranase was particularly pronounced for CGTase. For both BAN™ and CGTase, there was a synergistic effect of combining them with mutanase and dextranase, since use of BAN™ or CGTase alone did not provide a plaque reduction in this test.

Example 3

Enzyme protein dose response curves for plaque inhibition/prevention effect

Three oral microorganisms, *Streptococcus sobrinus*, *Actinomyces viscosus* and *Fusobacterium nucleatum*, respectively, were cultivated anaerobically overnight at 37° C. in the presence of various enzymes (Fungamyl™, Promozyme™ and Maltogenase™, all from Novo Nordisk A/S). Hydroxyapatite disks coated with sterilised saliva were immersed in a culture broth during cultivation so that an oral biofilm was formed on the disks. After cultivation, the disks were briefly rinsed with a phosphate-buffered saline and then incubated in a 1 ml 0.1% Erythrosin B solution in PBS for 1 minute to stain plaque present on the hydroxyapatite disks red. The Erythrosin B solution was removed and the disks were rinsed with PBS for a few minutes. The disks were air-dried overnight. Biofilm remaining on the disks was determined by measuring the intensity of the red colour (a*) using a Chromameter CR-200, the obtained values being compared to values for non-treated disks. The results are shown in the attached FIGS. 1, 2 and 3.

What is claimed is:

1. An oral care product comprising (a) a plaque-inhibiting or plaque-removing effective amount of an enzyme of E.C. 2.4.1 and (b) an abrasive polishing material, foaming agent, flavoring agent, humectant, binder, thickener, and/or sweetner, wherein the oral care product is a toothpaste, tooth gel, tooth powder or denture cleaning composition.

2. The oral care product of claim 1, wherein the enzyme is a cyclomaltodextrin glucanotransferase (EC 2.4.1.19).

3. The oral care product of claim 2, wherein the cyclomaltodextrin glucanotransferase is derived from a strain of *Bacillus autolyticus, Bacillus cereus, Bacillus circulans, Bacillus circulans var. alkalophilus, Bacillus coagulans, Bacillus firmus, Bacillus halophilus, Bacillus macerans, Bacillus megaterium, Bacillus ohbensis, Bacillus stearothermophilus, Bacillus subtilis, Klebsiella pneumoniae, Thermoanaerobacter sp., Thermoanaerobacter ethanolicus, Thermoanaerobacter finnii, Clostridium thermoamylolyticum, Clostridium thermosaccharolyticum,* or *Thermoanaerobacterium thermosulfurigenes.*

4. The oral care product of claim 1, wherein the enzyme is a transglucosidase (EC 2.4.1.18).

5. The oral care product of claim 4, wherein the transglucosidase is derived from *Aspergillus niger.*

6. The oral care product of claim 1, further comprising a starch-hydrolyzing enzyme.

7. The oral care product of claim 6, wherein the starch-hydrolyzing enzyme is an α-amylase.

8. The oral care product of claim 6, wherein the starch-hydrolyzing enzyme is a debranching enzyme.

9. The oral care product of claim 8, wherein the debranching enzyme is a pullulanase.

10. The oral care product of claim 1, further comprising a dextranase and/or a mutanase.

11. An oral care product comprising (a) a plaque-inhibiting or plaque-removing effective amount of an enzyme of E.C. 2.4.1 and (b) a wash/alcohol solution, flavoring agent, humectant, and/or sweetener, wherein the oral care product is a mouthwash.

12. The oral care product of claim 11, wherein the enzyme is a cyclomaltodextrin glucanotransferase (EC 2.4.1.19).

13. The oral care product of claim 12, wherein the cyclomaltodextrin glucanotransferase is derived from a strain of *Bacillus autolyticus, Bacillus cereus, Bacillus circulans, Bacillus circulans var. alkalophilus, Bacillus coagulans, Bacillus firmus, Bacillus halophilus, Bacillus macerans, Bacillus megaterium, Bacillus ohbensis, Bacillus stearothermophilus, Bacillus subtilis, Klebsiella pneumoniae, Thermoanaerobacter sp., Thermoanaerobacter ethanolicus, Thermoanaerobacter finnii, Clostridium thermoamylolyticum, Clostridium thermosaccharolyticum,* or *Thermoanaerobacterium thermosulfurigenes.*

14. The oral care product of claim 11, wherein the enzyme is a transglucosidase (EC 2.4.1.18).

15. The oral care product of claim 14, wherein the transglucosidase is derived from *Aspergillus niger.*

16. The oral care product of claim 11, further comprising a starch-hydrolyzing enzyme.

17. The oral care product of claim 16, wherein the starch-hydrolyzing enzyme is an α-amylase.

18. The oral care product of claim 16, wherein the starch-hydrolyzing enzyme is a debranching enzyme.

19. The oral care product of claim 18, wherein the debranching enzyme is a pullulanase.

20. The oral care product of claim 11, further comprising a dextranase and/or a mutanase.

21. An oral care product comprising (a) a plaque-inhibiting or plaque-removing effective amount of an enzyme of E.C.2.4.1 and (b) a chewing gum base, wherein the oral care product is a chewing gum.

22. The oral care product of claim 21, wherein the enzyme is a cyclomaltodextrin glucanotransferase (EC 2.4.1.19).

23. The oral care product of claim 22, wherein the cyclomaltodextrin glucanotransferase is derived from a strain of *Bacillus autolyticus, Bacillus cereus, Bacillus circulans, Bacillus circulans var. alkalophilus, Bacillus coagulans, Bacillus firmus, Bacillus halophilus, Bacillus macerans, Bacillus megaterium, Bacillus ohbensis, Bacillus stearothermophilus, Bacillus subtilis, Klebsiella pneumoniae, Thermoanaerobacter sp., Thermoanaerobacter ethanolicus, Thermoanaerobacter finnii, Clostridium thermoamylolyticum, Clostridium thermosaccharolyticum,* or *Thermoanaerobacterium thermosulfurigenes.*

24. The oral care product of claim 21, wherein the enzyme is a transglucosidase (EC 2.4.1.18).

25. The oral care product of claim 24, wherein the transglucosidase is derived from *Aspergillus niger.*

26. The oral care product of claim 21, further comprising a starch-hydrolyzing enzyme.

27. The oral care product of claim 26, wherein the starch-hydrolyzing enzyme is an α-amylase.

28. The oral care product of claim 26, wherein the starch-hydrolyzing enzyme is a debranching enzyme.

29. The oral product of claim 28, wherein the debranching enzyme is a pullulanase.

30. The oral care product of claim 21, further comprising a dextranase and/or a mutanase.

31. A dental floss, toothpick, or lozenge comprising a plaque-inhibiting or plaque-removing effective amount of an enzyme of E.C.2.4.1.

32. The dental floss, toothpick, or lozenge of claim 31, wherein the enzyme is a cyclomaltodextrin glucanotransferase (EC2.4.1.19).

33. The dental floss, toothpick, or lozenge of claim 32, wherein the cyclomaltodextrin glucanotransferase is derived from a strain of *Bacillus autolyticus, Bacillus cereus, Bacillus circulans, Bacillus circulans var. alkalophilus, Bacillus coagulans, Bacillus firmus, Bacillus halophilus, Bacillus*

*macerans, Bacillus megaterium, Bacillus ohbensis, Bacillus stearothermophilus, Bacillus subtilis, Klebsiella pneumoniae, Thermoanaerobacter sp., Thermoanaerobacter ethanolicus, Thermoanaerobacter finnii, Clostridium thermoanmylolyticum, Clostridium thermosaccharalyticum,* or *Thermoanaerobacterium thermosulfurigenes.*

34. The dental floss, toothpick, or lozenge of claim 31, wherein the enzyme is a transglucosidase (EC2.4.1.18).

35. The dental floss, toothpick, or lozenge of claim 34, wherein the transglucosidase is derived from *Aspergillus niger.*

36. The dental floss, toothpick, or lozenge of claim 31, further comprising a starch-hydrolyzing enzyme.

37. The dental floss, toothpick, or lozenge of claim 36, wherein the starch-hydrolyzing enzyme is an α-amylase.

38. The dental floss, toothpick, or lozenge of claim 37, wherein the starch-hydrolyzing enzyme is a debranching enzyme.

39. The dental floss, toothpick, or lozenge of claim 38, wherein the debranching enzyme is a pullulanase.

40. The dental floss, toothpick, or lozenge of claim 31, further comprising a dextranase and/or a mutanase.

* * * * *